United States Patent [19]

Hazony et al.

[11] Patent Number: 4,649,749

[45] Date of Patent: Mar. 17, 1987

[54] ULTRASONIC TRANDUCER

[75] Inventors: Dov Hazony, University Heights; Richard E. Berris, Jr., Bainbridge Township, Ross County, both of Ohio

[73] Assignee: J. W. Harley Pump Works, Inc., Twinsburg, Ohio

[21] Appl. No.: 702,926

[22] Filed: Feb. 19, 1985

[51] Int. Cl.$^4$ ............................................. G01N 29/00
[52] U.S. Cl. ...................................... 73/597; 310/336; 73/632
[58] Field of Search ................ 73/629, 632, 597, 599, 73/622, 637, 638, 593, 660; 310/334, 335, 336, 322, 326, 327

[56] References Cited

U.S. PATENT DOCUMENTS

| | | | |
|---|---|---|---|
| 2,460,153 | 1/1949 | Smoluchowski | 310/336 |
| 2,803,129 | 8/1957 | Bradfield | 310/327 |
| 3,376,438 | 4/1968 | Colbert | 310/327 |
| 3,543,065 | 11/1970 | Phelan | 310/336 |
| 3,994,154 | 11/1976 | Niklas et al. | 73/597 |
| 4,041,773 | 8/1977 | Hauldren et al. | 73/638 |
| 4,217,781 | 8/1980 | Abts | 310/334 |
| 4,505,160 | 3/1985 | Zacharias, Jr. | 310/336 |
| 4,510,793 | 4/1985 | Ploegaert et al. | 73/597 |

*Primary Examiner*—Stephen A. Kreitman
*Attorney, Agent, or Firm*—James A. Hudak

[57] ABSTRACT

An ultrasonic piezoelectric transducer and a method for measuring and/or monitoring the thickness of a wear member, in-situ, and the amount of wear that has occurred thereto, is disclosed. The transducer includes a sleeve which is received in a blind bore provided in the wear member, a piezoelectric element positioned within the blind bore, and an aligning spacer means interposed between the end of the sleeve and the piezoelectric element. By the application of appropriate voltage pulses to the piezoelectric element, the wall thickness between the bottom of the blind bore and the inner surface of the wear member can be measured.

32 Claims, 5 Drawing Figures

ULTRASONIC TRANDUCER

TECHNICAL FIELD

The present invention relates to a method for measuring and/or monitoring the thickness of a wear member and the amount of wear that has occurred thereto, and more particularly to an ultrasonic piezoelectric transducer for measuring and/or monitoring such thickness and wear.

BACKGROUND ART

Various approaches have been devised for detecting, monitoring and measuring the amount of wear which has occurred to a wear member. For example, in the area of rotating equipment, a number of electrical devices are available to detect and monitor bearing wear. These devices are based upon a number of detection techniques. Thus, wear detection might depend upon the completion of an electrical circuit through the bearing when there is excessive bearing wear, or it might depend upon the generation of a voltage if the shaft rotates eccentrically, or it might depend upon the detection of an abnormal temperature rise of the bearing. Each of these approaches has some inherent disadvantages with respect to accuracy and does not measure actual bearing wear or bearing wall thickness, i.e., each approach is responsive to bearing wear but does not measure quantitatively the amount of wear that has occurred or the wall thickness remaining.

Other approaches have been devised to measure the thickness of a workpiece or wear member, and by measuring such thickness, the amount of wear which has occurred can be calculated. These approaches have numerous commercial and/or industrial applications, however, their use for measuring the wear of a work surface in-situ is cost prohibitive. In addition, these approaches typically utilize devices fabricated from materials which limit their applications to an operating environment having a temperature of normally less than 75° C., and cause the resulting readings to be dependent upon the temperature of the operating environment. It has also been found that the materials utilized for these devices cannot withstand severe operating environments which further limits the applications in which they can be used. Thus, these devices and measurement techniques are not usable for measuring and/or monitoring the thickness of work surfaces, such as a sleeve bearing, in an elevated temperature operating environment such as might exist in rotating equipment. This inability to measure and/or monitor bearing wear in-situ can result in costly machine downtime to inspect the condition of the bearings. Alternatively, this inability can result in unnecessary damage to the rotating equipment due to bearing failure which was not promptly detected.

Because of the foregoing, it has become desirable to develop a device which can be utilized to measure and/or monitor the thickness of and the amount of wear which has occurred to sleeve or thrust bearings, brake discs or pads, clutch plates and sealing members, in-situ.

SUMMARY OF THE INVENTION

The present invention provides an ultrasonic piezoelectric transducer that can be mounted within the wall of a wear member, such as a sleeve or thrust bearing, brake disc or pad, clutch plate or sealing device, so that measurements of wall thickness can be made in-situ. The transducer includes an outer sleeve which is threadedly received in a blind bore within the wear member, a piezoelectric element which is positioned within the blind bore, and spacer means interposed between the end of the outer sleeve and the piezoelectric element. The spacer means and the end of the outer sleeve have complementary configurations permitting the spacer means to align itself within the end of the outer sleeve and apply a substantially uniform compressive force to the piezoelectric element. The application of such a substantially uniform compressive force causes a firm, electro-acoustical contact to be formed between the piezoelectric element and the bottom of the blind bore which insures a highly accurate measurement of the wall thickness between the bottom of the blind bore and the inner surface of the wear member. For example, it has been found experimentally that this transducer can measure the wall thickness (0.100 inch) of a bronze bearing at 300° F. with a repeatability in the sub-micron range utilizing state-of-the-art electronics. The transducers can also be located in a pre-determined arrangement around the periphery of the wear member so that wear can be measured and/or monitored around the periphery thereof.

In an alternate embodiment of the invention, a mounting ring is provided to position one or more transducers against the outer surface of the wear member. In this embodiment, the piezoelectric elements contact the outer surface of the wear member and the total thickness of the wear member is measured.

In still another alternate embodiment of the invention, the blind bores within the wear member are replaced with through bores to reduce production costs. A transducer assembly is received within each of the through bores so that its end is flush with the inner surface of the wear member. In this embodiment, the end of the transducer assembly is actually a part of the wear surface and the thickness of the end of the transducer assembly is being measured.

Regardless of the embodiment utilized, a separate transducer may be placed in the same environment as the other transducers for use as a relevant time reference.

DESCRIPTION OF THE PREFERRED EMBODIMENT

Figure 1:
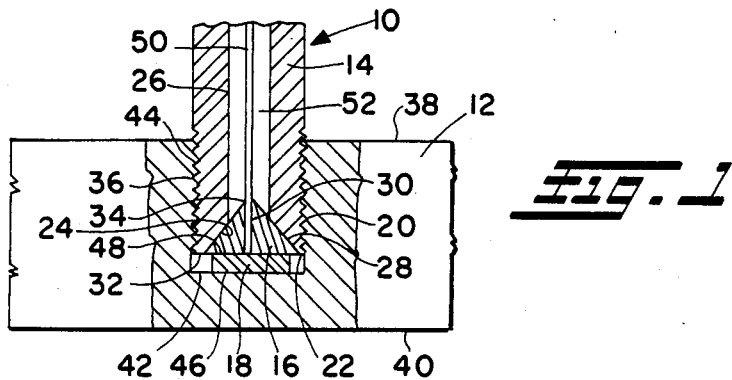
FIG. 1 is a partial cross-sectional view of an ultrasonic piezoelectric transducer embodying the invention of this disclosure and installed in a wear member.

Referring now to the drawings where the illustrations are for the purpose of describing the preferred embodiment of the present invention and are not intended to limit the invention hereto, FIG. 1 is a cross-sectional view of the transducer 10 installed in a wear member 12, such as a sleeve or thrust bearing, clutch plate, brake disc or pad, sealing member or the like, whose thickness is to be measured and/or monitored. The transducer 10 is comprised of an outer sleeve 14, an aligning and electrically insulating spacer 16 received within the end of the outer sleeve, and a piezoelectric element 18.

The outer sleeve 14 is fabricated from round tubing, such as brass tubing or the like, which has threads 20 formed adjacent one end thereof. Typically, the tubing material has the same or similar thermal expansion properties as that of the wear member 12 to maintain a firm contact therewith. This firm contact is provided by the threads 20 which engage complementary threads provided in the wear member 12, as hereinafter described. The threads 20 also permit the adjustment of the outer sleeve 14 within the wear member 12 to optimize the operation of the transducer 10 as later discussed. It should be noted that other approaches are possible for the adjustable attachment of the outer sleeve 14 to the wear member 12, such as a bracket arrangement (not shown) that is adjustable with respect to the wear member 12 and which retains the sleeve 14. The end 22 of the outer sleeve 14 has an indentation provided therein forming a surface 24 connecting the end 22 of the sleeve 14 with the inner circumferential wall 26 of the sleeve. This indentation may have a curved configuration, such as semispherical or parabolic, or it may have a conical configuration which is preferred to permit alignment of the spacer 16 therein.

The aligning and electrically insulating spacer 16 is fabricated from a ceramic or ceramic-like material that is capable of sustaining high temperatures and high pressures. For example, pyrolytic boronitride or another ceramic-like material can be used for the spacer 16. The particular ceramic or ceramic-like material utilized for the spacer 16 is selected to compensate for the thermal expansion properties of the other components comprising the transducer 10 and the wear member 12 so that the spacer 16 will maintain a substantially uniform compressive force on the piezoelectric element 18 over a broad operating temperature range. The spacer 16 typically has a conical configuration that is complementary to that of the indentation formed in the end 22 of the outer sleeve 14. The spacer 16 is received within the indentation so that the outer surface 28 defining its conical configuration contacts the surface 24 formed by the indentation. The use of conical surfaces 24, 28 formed on the outer sleeve 14 and the spacer 16, respectively permits the alignment of the spacer 16 within the outer sleeve 14 through elastic deformation of the spacer 16 and the indentation formed in the end 22 of the outer sleeve 14. In contrast, self-alignment of the spacer 16 within the outer sleeve 14 can be achieved by using a semi-spherical or parabolic configuration for the surfaces 24, 28 formed on the end 22 of the outer sleeve 14 and the spacer 16, respectively. It should be noted that regardless of the shape of the complementary configurations used for the spacer 16 and the indentation in the end 22 of the outer sleeve 14, a precise fit of the spacer 16 within the indentation is not necessary since any deviations in size or shape will be compensated for by the elastic deformation of the spacer 16 and the indentation and/or by the self-alignment of the complementary curved surfaces. The alignment of the spacer 16 within the outer sleeve 14, whether by elastic deformation of the spacer 16 and the indentation in the end 22 of the outer sleeve 14 or by self-alignment through complementary curved surfaces, is necessary to ensure the application of a uniform compressive force on the piezoelectric element 18. Such a substantially uniform compressive force also minimizes the possibility of damaging the piezoelectric element 18 through the application of a nonuniform compressive force thereto. Even though both of the foregoing approaches apply a substantially uniform compressive force to the piezoelectric element 18, it has been found that the use of an appropriate conical configuration for the spacer 16 and the indentation in the end 22 of the outer sleeve 14 is easier to implement and may result in a substantially higher absorption and obliteration of spurious echoes from the primary ultrasonic signal than if complementary curved configurations are used for the spacer 16 and the indentation in the end 22 of the outer sleeve 14. Thus, the use of a conical configuration for the spacer 16 and the end 22 of the outer sleeve 14 results in a higher signal to noise ratio than if complementary curved configurations are used for same. In summary, the spacer 16 is necessary in this structure in order to provide a substantially uniform compressive force to the piezoelectric element 18 and to absorb and obliterate spurious echoes. Regardless of the configuration utilized for the spacer 16, an aperture 30 is formed therethrough. This aperture is sufficiently large to permit the passage of an electric conductor therethrough.

The wear member 12 whose thickness is to be measured and/or monitored is provided with a blind bore 36 therein. The blind bore 36 is located so as to be substantially perpendicular to the outer and inner surfaces 38, 40, respectively of the member 12. If the member 12 is a sleeve bearing, the blind bore 36 is directed radially inwardly so as to be perpendicular to tangents which intersect its centerline on the outer and inner surfaces 38, 40 of the member 12. The blind bore 36 is of a predetermined depth and has a substantially flat surface 42 at the bottom thereof. The distance between the flat surface 42 and the inner surface 40 of the member 12 is the distance to be measured and/or monitored. The blind bore 36 may also have threads 44 formed therein which terminates adjacent the bottom thereof.

The piezoelectric element 18 is a standard state-of-the-art device and typically has a round disc-like shape. The element 18 can be formed from commercially available piezoelectric transducer material, such as PZT-5H available from Vernitron, Inc. of Bedford, Ohio. The size of the element 18 is a function of the overall size of the transducer 10, however, an element having a diameter of 0.080 inch and a thickness of 0.003 inch has been tested experimentally with excellent results. The diameter of the element 18 is slightly less than the diameter of the blind bore 36 provided in the wear member 12. The element 18 is responsive to a short voltage pulse, such as a 200 volt DC pulse of 10 nanosecond duration, and converts the voltage pulse into a pressure pulse which is applied to the surface of the material whose thickness is to be measured and/or monitored. Similarly, the piezoelectric element 18 converts the "echo" return pressure pulse from the opposite surface of the material whose thickness is being monitored into a voltage pulse for measurement purposes. The substantially uniform compressive force applied to the piezoelectric element 18 by the spacer 16 ensures that the element 18 is firmly "seated" within the blind bore 36 for the proper transmission of the voltage pulse into the element 18 and the reception of the reflected "echo" pulse by the element.

In order to assemble the transducer 10, the piezoelectric element 18 is received within the blind bore 36 and positioned so that one side 46 thereof contacts the flat surface 42 at the bottom of the blind bore 36. Inasmuch as the diameter of the element 18 is only slightly less than the diameter of the blind bore 36, the center of the element 18 and the center of the flat surface 42 at the bottom of the blind bore 36 will substantially coincide, however, such coincidence is not necessary for the proper operation of the transducer 10. The other side 48 of the piezoelectric element 18 may be soldered to an electrical conductor 50. The electrical conductor 50 is received through the aperture 30 provided in the spacer 16, and the spacer 16 is received in the blind bore 36 so that its base 32 contacts the side 48 of the piezoelectric element 18 which is mechanically and electrically connected to the electrical conductor 50. The threads 20 on the outer sleeve 14 are coated with an adhesive, such as Loctite, and the sleeve 14 is threadedly advanced into the wear member 12 until the conical surface 24 provided on its end 22 engages the outer surface 28 of the spacer 16. Further advancement of the outer sleeve 14 into the wear member 12 causes the elastic deformation of the spacer 16 and the indentation in the end 22 of the outer sleeve 14, and the application of a substantially uniform compressive force by the base 32 of the spacer 16 to the side 48 of the piezoelectric element 18. If complementary curved configurations, such as semispherical or parabolic, are used for the spacer 16 and the indentation in the end 22 of the outer sleeve 14, the spacer 16 will self-align itself within the indentation in the end 22 of the outer sleeve 14 so that its base 32 will apply a substantially uniform compressive force to the side 48 of the piezoelectric element 18. Regardless of the shape of the spacer 16 and the indentation in the end 22 of the outer sleeve 14, the outer sleeve 14 is threadedly advanced into the wear member 12 by manually rotating the outer sleeve 14 until a snug fit exists between the indentation provided in its end 22 and the outer surface 28 of the spacer 16, and between the base 32 of the spacer 16 and the side 48 of the piezoelectric element 18. In order to ensure that such a snug fit exists, the foregoing advancement of the outer sleeve 14 into the wear member 12 is monitored by a pulser-receiver device and an oscilloscope (all not shown). With this apparatus a series of short voltage pulses is applied by the pulser to the transducer 10 while the outer sleeve 14 is being threadedly advanced into the wear member 12 so that the sleeve 14 can be rotationally adjusted until the optimum return "echo" pulse, shown on the oscilloscope, is received by the receiver. In this manner, a snug fit between the foregoing components is assured and the transducer 10 and the wear member 12 are "tuned" to provide the optimum return "echo" pulse.

Since the piezoelectric element 18 is somewhat formable under a compressive force, the application of a substantially uniform compressive force thereto results in a firm, optimum electro-acoustical contact between the side 46 of the element 18 and the flat surface 42 at the bottom of the blind bore 36. By providing such a firm, optimum electro-acoustical contact with the flat surface 42 of the blind bore 36, any signals emanating from the piezoelectric element 18 will be properly directed toward the inner surface 40 of the wear member 12 to be measured and/or monitored, and the wear member 12 will provide the proper electrical ground for the system. Thus, the surfaces 24, 28 compensate for deviations in manufacturing tolerances in the components involved, and the possibility that the blind bore 36 may not be positioned exactly normal to the inner surface 40 of the wear member 12. Both of these conditions could result in the piezoelectric element 18 not firmly contacting the flat surface 42 of the blind bore 36 which, in turn, could result in inaccurate measurements and/or system malfunctions. After the transducer 10 has been assembled and installed in the wear member 12, the area 52 enclosed by the inner circumferential wall 26 of the outer sleeve 14 and containing the electrical conductor 50 may be filled with a dense insulating and dampening material such as epoxy, e.g., Duro epoxy, loaded with tungsten for application temperatures less than 400° F. or a loaded ceramic adhesive for temperatures in excess of 400° F. This electric insulation material and the spacer 16 preferably match the acoustical impedance of the piezoelectric element 18 and help suppress spurious echoes, which are later in time and thus much weaker than the primary ultrasonic pressure pulse, from interferring with the primary pulse. After the installation of the transducer 10 in the wear member 12 has been completed, an epoxy may be placed on the outer surface of the sleeve 14 adjacent the top surface of the wear member 12 to prevent any contaminants from entering the transducer.

Figure 2:
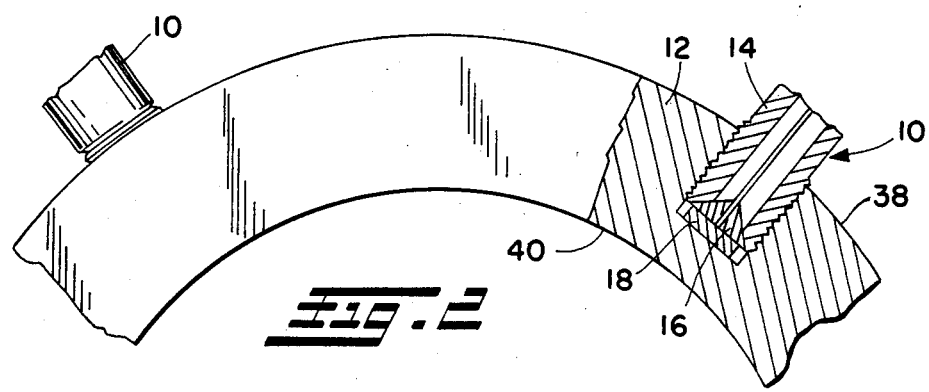
FIG. 2 is a partial cross-sectional view of a plurality of ultrasonic piezoelectric transducers embodying the invention of this disclosure and installed in and around the periphery of a wear member, such as a sleeve bearing.

The wear member 12 may have a configuration that is either flat, such as a brake disc, clutch plate, face type seal or thrust type bearing, or circular, such as a sleeve bearing or ring type seal. In any case, a plurality of transducers can be utilized to measure and/or monitor wear at various locations on the wear member 12. If a sleeve bearing is utilized, the plurality of transducers 10 can be placed within the outer bearing wall and around the periphery of the bearing, as shown in FIG. 2. In this manner, bearing wear can be measured and/or monitored around the periphery thereof. Thus, by placing the transducer 10 within one or more blind bores 36 within the bearing, wear can be measured and/or monitored in-situ, eliminating costly periodic machine downtime to inspect the condition of the bearing. Machine downtime would only occur when a transducer indicates that sufficient wear has occurred to justify the replacement of the bearing.

Figure 3:
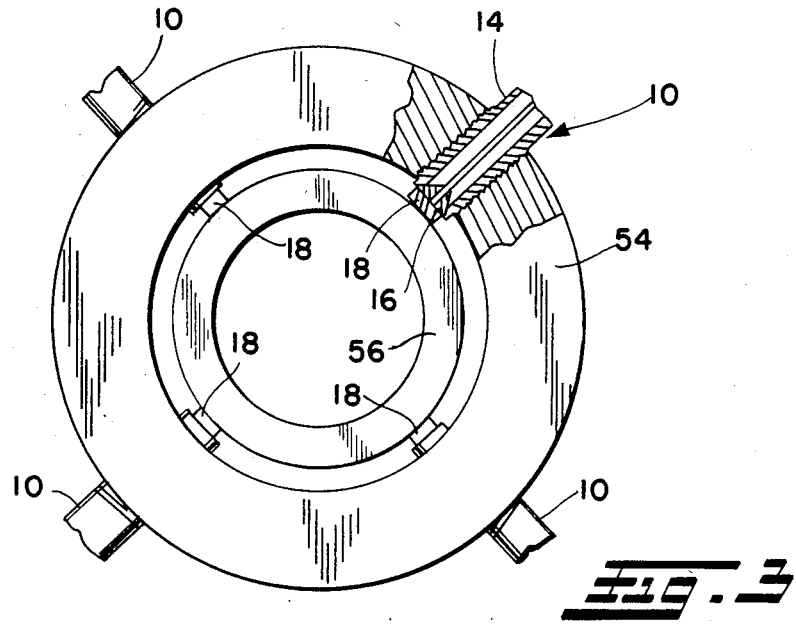
FIG. 3 is a partial cross-sectional view of a mounting ring for retaining one or more ultrasonic piezoelectric transducers against the outer surface of a wear member, such as a sleeve bearing.

Alternatively, rather than placing a plurality of transducers 10 within the blind bores provided in the outer bearing wall, a mounting attachment 54, such as a ring as shown in FIG. 3, could be used to retain the transducers 10 in a radially spaced apart relationship. In such an arrangement, the mounting attachment 54 would be slipped over the sleeve bearing 56 and the piezoelectric elements 18 would firmly contact the outer surface of the bearing wall. Thus, no blind bores would be required in the bearing wall. In this arrangement, since the radius of the curvature of the bearing 56 is substantially greater than the diameter of each piezoelectric element 18 and inasmuch as a substantial compressive force is being applied to each element 18 by its associated spacer 16, it has been found that sufficient surface contact exists between each element 18 and the outer surface of the bearing 56 to produce very accurate distortionless measurements of wall thickness. Thus, by using this apparatus, the total bearing wall thickness can be measured and/or monitored at various locations on the bearing.

In addition to being able to measure wear in-situ, the construction of the transducer 10 provides another advantage in that no buffer element is required between the piezoelectric element 18 and the wall whose thickness is being measured and/or monitored, i.e., the distance between the flat surface 42 of the blind bore 36 and the inner surface 40 of the wear member 12. Typically, in prior art devices such a buffer element is required for mechanical support, impedance matching and sealing of the transducer, however, its use greatly attenuates and degrades the primary pulses produced by the transducer and the reflected "echo" pulses received by the transducer. Inasmuch as the transducer 10 requires no buffer element, such signal attenuation and degradation does not occur. In addition, because of the absence of a buffer element, a firm electrical and acoustical contact can be made by the piezoelectric element 18 directly to the wall thickness being measured and/or monitored, and the resulting measurements have a much higher degree of accuracy than those resulting from prior art devices. For example, measurements with a repeatability in the sub-micron range utilizing state-of-the-art electronics have been achieved. And lastly, due to the inherent simplicity of the structure of the transducer, it is substantially less costly to produce than the prior art devices.

Figure 4:
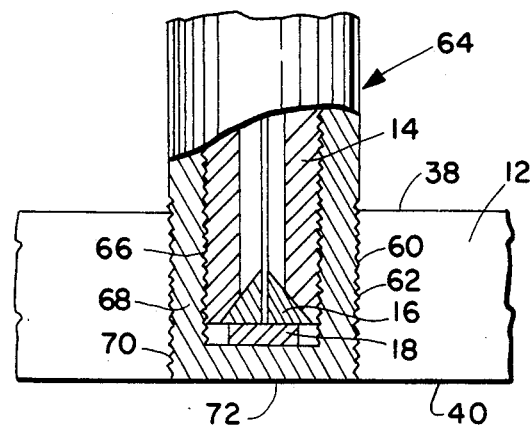
FIG. 4 is a partial cross-sectional view of an alternate embodiment of an ultrasonic piezoelectric transducer embodying the invention of this disclosure and installed in a wear member.

In an alternate embodiment of the invention, as shown in FIG. 4, the blind bore 36 in the wear member 12 is replaced with a through bore 60 connecting the outer and inner surfaces 38, 40 of the member 12. The through bore 60 may have threads 62 formed therein. A transducer 64 comprising an outer sleeve 14, a spacer 16, and a piezoelectric element 18 is received within a blind bore 66 in a wear reference member 68 which may have threads 70 formed on the outer surface thereof. The wear reference member 68 is received within the through bore 60 so that its end 72 is substantially flush with the inner surface 40 of the wear member 12. The inner surface 40 of the wear member 12 is then machined to ensure that the end 72 of the wear reference member 68 is flush with the inner surface 40. It should be noted that the material utilized for the wear reference member 68 may be the same as or may be different from the material comprising the wear member 12 inasmuch as only the thickness of the end of the reference member 68 is being monitored and/or measured. The operation of this embodiment is similar to the previous embodiment utilizing a blind bore, however, it is easier and less costly to produce.

Figure 5:
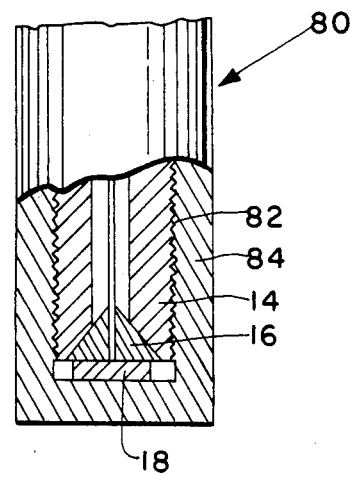
FIG. 5 is a cross-sectional view of an ultrasonic piezoelectric transducer used as a relevant time reference.

With any of the foregoing embodiments, it might be desired to compensate for the temperature and pressure of the environment, the density of the material utilized for the transducer, and the strains existing on the transducer. Such compensation can be accomplished by using a time reference transducer 80, as shown in FIG. 5. The structure of this transducer 80 is similar to transducer 10, in that it is comprised of an outer sleeve 14, a spacer 16, and a piezoelectric element 18, however, the foregoing components are received in a blind bore 82 provided in a reference member 84, which is similar to wear reference member 68. The material utilized for the reference member 84 is the same as or similar to the material for the wear member 12 if a blind bore 36 is utilized in the member 12, or the same as or similar to the material for the wear reference member 68 if a through bore 60 is provided in the wear member 12. The assembly of the transducer 80 and the reference member 84 is placed within the same temperature, pressure or material environment as the other transducers 10, though not necessarily contacting the wear member 12. By monitoring the measurements of the reference distance, produced by the transducer 80, the measurements produced by the transducers 10 can be adjusted to compensate for possible measurement variations caused by operating environment changes.

Certain modifications and improvements will occur to those skilled in the art upon reading the foregoing. It should be understood that all such modifications and improvements have been deleted herein for the sake of conciseness and readability, but are properly within the scope of the following claims.

We claim:

1. An ultrasonic transducer device for measuring the thickness of a member comprising a piezoelectric element and means for biasing said piezoelectric element against a surface of the member whose thickness is to be measured, said biasing means comprising a sleeve having a recess provided in one end thereof and spacer means received within said recess in said sleeve so that a portion of the surface defining said recess contacts a portion of the surface of said spacer means, said recess and said spacer means having complementary non-linear configurations and said contacting surface portions on said recess and said spacer means both having substantially continuous configurations permitting the alignment of said spacer means within said recess, said spacer means also having a substantially flat surface thereon which contacts said piezoelectric element and applies a substantially uniform force across the entire surface of said piezoelectric element.

2. The transducer device as defined in claim 1 wherein said piezoelectric element has a pair of faces, one of said pair of faces being on contact with a surface of the member whose thickness is to be measured and the other of said pair of faces being compressed by said spacer means.

3. The transducer device as defined in claim 2 further including an electrical conductor operatively connected to said piezoelectric element, said electrical conductor being received through said sleeve and said spacer means for connection to said piezoelectric element.

4. The transducer device as defined in claim 3 wherein said electrical conductor is operatively connected to said other of said pair of faces of said piezoelectric element.

5. The transducer device as defined in claim 3 further including insulating means received within said sleeve, said insulating means being positioned so as to be in a surrounding relationship with said electrical conductor.

6. The transducer device as defined in claim 5 wherein said insulating means comprises a material which substantially matches the acoustical impedance of the transducer device.

7. The transducer device as defined in claim 1 wherein said surface defining said recess in said sleeve has a conical configuration which contacts the surface of said spacer means.

8. The transducer device as defined in claim 1 wherein the surface of said spacer means has a conical configuration which contacts said surface defining said recess in said sleeve.

9. The transducer as defined in claim 1 wherein said complementary non-linear configurations are conical in shape.

10. The transducer as defined in claim 9 wherein said conical complementary configurations for said recess and said spacer means permit said spacer means to be aligned within said recess through elastic deformation of said spacer means.

11. The transducer as defined in claim 1 wherein said complementary non-linear configurations are curved in shape.

12. The transducer device as defined in claim 11 wherein said curved complementary configurations for said recess and said spacer means permit said portion of said surface of said spacer means to slidingly engage said portion of said surface defining said recess in said sleeve allowing self-alignment of said spacer means within said recess.

13. The transducer device as defined in claim 1 wherein said sleeve has threads formed on the outer surface thereof adjacent said one end thereof, said threads permitting the attachment of said transducer device to a member whose thickness is to be measured.

14. A device for measuring the thickness of a member in-situ comprising, in combination, a piezoelectric element, a member whose thickness is to be measured, and means for biasing said piezoelectric element against a surface of said member whose thickness is to be measured, said biasing means comprising a sleeve having a recess provided in one end thereof and spacer means received with said recess in said sleeve so that a portion of the surface defining said recess contacts a portion of the surface of said spacer means, said recess and said spacer means having complementary non-linear configurations and said contacting surface portions on said recess and said spacer means both having substantially continuous configurations permitting the alignment of said spacer means within said recess, said spacer means also having a substantially flat surface thereon which contacts said piezoelectric element and applies a substantially uniform force across the entire surface of said piezoelectric element.

15. The combination as defined in claim 14 wherein said piezoelectric element has a pair of faces, one of said pair of faces being in contact with said member whose thickness is to be measured and the other of said pair of faces being compressed by said spacer means.

16. The combination as defined in claim 15 wherein said member has a blind bore provided therein, said piezoelectric element being received within said blind bore allowing said one of said pair of faces of said piezoelectric element to contact the bottom surface of said blind bore.

17. The combination as defined in claim 15 further including an electrical conductor operatively connected to said piezoelectric element, said electrical conductor being received through said sleeve and said spacer means for connection to said piezoelectric element.

18. The combination as defined in claim 17 wherein said electrical conductor is operatively connected to said other of said pair of faces of said piezoelectric element.

19. The combination as defined in claim 17 further including insulating means received within said sleeve, said insulating means being positioned so as to be in a surrounding relationship with said electrical conductor.

20. The combination as defined in claim 19 wherein said insulating means comprises a material which substantially matches the acoustical impedance of the transducer device.

21. The combination as defined in claim 14 wherein said surface defining said recess in said sleeve has a conical configuration which contacts the surface of said spacer means.

22. The combination as defined in claim 14 wherein the surface of said spacer means has a conical configuration which contacts said surface defining said recess in said sleeve.

23. The combination as defined in claim 14 wherein said complementary non-linear configurations are conical in shape.

24. The combination as defined in claim 23 wherein said conical complementary configurations for said recess and said spacer means permit said spacer means to be aligned within said recess through elastic deformation of said spacer means.

25. The combination as defined in claim 14 wherein said complementary non-linear configurations are curved in shape.

26. The combination as defined in claim 25 wherein said curved complementary configurations for said recess and said spacer means permit said portion of said surface of said spacer means to slidingly engage said portion of said surface defining said recess in said sleeve allowing self-alignment of said spacer means within said recess.

27. The combination as defined in claim 14 wherein said member whose thickness is to be measured provides conductive properties and the electrical ground for the combination.

28. A device for measuring the thickness of a member in-situ at various locations thereon comprising, in combination, a plurality of piezoelectric elements, a member whose thickness is to be measured at various locations thereon, and means for biasing one of said plurality of piezoelectric elements against said member so as to contact said member at each of said measurement locations, said baising means comprising a sleeve having a recess provided in one end thereof and spacer means received within said recess in said sleeve so that a portion of the surface defining said recess contacts a portion of the surface of said spacer means, said recess and said spacer means having complementary non-linear configurations and said contacting surface portions on said recess and said spacer means both having substantially continuous configurations permitting the alignment of said spacer means within said recess, said spacer means also having a substantially flat surface thereon which contacts said piezoelectric element and applies a substantially uniform force across the entire surface of said piezoelectric element.

29. The combination as defined in claim 28 wherein said various measurement locations on said member are in a pre-determined arrangement.

30. The combination as defined in claim 28 wherein said member provides conductive properties and the electrical ground for the combination.

31. A method for measuring the thickness of a member in-situ through the use of an ultrasonic transducer device comprising a piezoelectric element and means for biasing said piezoelectric element against a surface of the member whose thickness is being measured, said biasing means comprising a sleeve having a recess provided in one end thereof and spacer means received within said recess in said sleeve so that a portion of the surface defining said recess contacts a portion of the surface of said spacer means, said recess and said spacer means having complementary non-linear configurations and said contacting surface portions on said recess and said spacer means both having substantially continuous configurations permitting the alignment of said spacer means within said recess, said spacer means also having a substantially flat surface thereon which contacts said piezoelectric element and applies a substantially uniform force across the entire surface of said piezoelectric element, said method comprising the steps of:

- locating said ultrasonic transducer device within the member whose thickness is being measured;
- applying a pulse to said ultrasonic transducer device causing said piezoelectric element to transmit an interrogating signal into the member whose thickness is being measured;
- receiving a return signal from the member whose thickness is being measured in response to said interrogating signal; and
- processing said interrogating signal and said return signal to determine the thickness of the member.

32. A method for determining the amount of wear which has occurred to a member in-situ by measuring the change in thickness of the member over a period of time through the use of an ultrasonic transducer device comprising a piezoelectric element and means for biasing said piezoelectric element against a surface of the member whose change in thickness is being measured, said biasing means comprising a sleeve having a recess provided in one end thereof and spacer means received within said recess in said sleeve so that a portion of the surface defining said recess contacts a portion of the surface of said spacer means, said recess and said spacer means having complementary non-linear configurations and said contacting surface portions on said recess and said spacer means both having substantially continuous configurations permitting the alignment of said spacer means within said recess, said spacer means also having a substantially flat surface thereon which contacts said piezoelectric element and applies a substantially uniform force across the entire surface of said piezoelectric element, said method comprising the steps of:

- locating said ultrasonic transducer device within the member whose change in thickness is being measured;
- applying a pulse to said ultrasonic transducer device causing said piezoelectric element to transmit a first interrogating signal into the member;
- receiving a first return signal from the member in response to said first interrogating signal;
- processing said first interrogating signal and said first return signal to determine a first thickness of the member;
- applying a pulse to said ultrasonic transducer device causing said piezoelectric element to transmit a second interrogating signal at a later time into the member;
- processing said second interrogating signal and said second return signal to determine a second thickness of the member; and
- processing said first thickness determination and said second thickness determination to determine the change in thickness which has occurred to the member.

* * * * *